United States Patent
Fu et al.

(10) Patent No.: US 7,049,334 B2
(45) Date of Patent: May 23, 2006

(54) ENHANCEMENT OF LEARNING AND MEMORY AND TREATMENT OF AMNESIA

(75) Inventors: Wen-Mei Fu, Taipei (TW); Keng-Chen Liang, Taipei (TW); Wei-Lin Chien, Taipei (TW); Sheng-Chu Kuo, Taichung (TW); Fang-Yuan Lee, Taichung (TW); Che-Ming Teng, Taipei (TW)

(73) Assignee: Carlsbad Technology, Inc., Carlsbad, CA (US)

( * ) Notice: Subject to any disclaimer, the term of this patent is extended or adjusted under 35 U.S.C. 154(b) by 403 days.

(21) Appl. No.: 10/242,826

(22) Filed: Sep. 13, 2002

(65) Prior Publication Data
US 2003/0105149 A1 Jun. 5, 2003

Related U.S. Application Data

(60) Provisional application No. 60/322,389, filed on Sep. 14, 2001.

(51) Int. Cl.
*A61K 31/416* (2006.01)

(52) U.S. Cl. ............. 514/406; 514/443; 514/469; 514/471; 514/412; 514/427; 514/405; 514/256

(58) Field of Classification Search ........... 514/406, 514/443, 469, 412, 427, 471, 405, 256
See application file for complete search history.

(56) References Cited

U.S. PATENT DOCUMENTS

| | | | |
|---|---|---|---|
| 5,240,947 A * | 8/1993 | Kuo et al. | 514/364 |
| 5,574,168 A | 11/1996 | Kuo et al. | 548/360.5 |
| 6,162,819 A * | 12/2000 | Schindler et al. | 514/405 |
| 6,693,102 B1 * | 2/2004 | Stasch et al. | 514/256 |

FOREIGN PATENT DOCUMENTS

WO   WO 200116359 A2 *   3/2001
WO   WO 200154771 A2 *   8/2001

* cited by examiner

*Primary Examiner*—Christopher S. F. Low
*Assistant Examiner*—Brian-Yoy S. Kwon
(74) *Attorney, Agent, or Firm*—Fish & Richardson P.C.

(57) ABSTRACT

A method for enhancing learning and memory or treating amnesia. The method includes administrating to a subject in need thereof a compound of the formula (I):

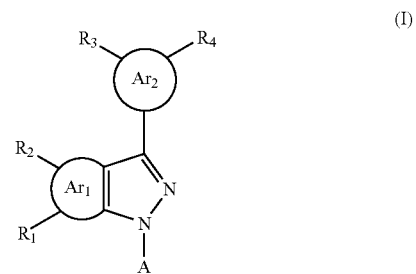

A is H, R, or

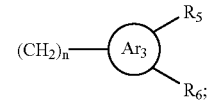

each of $Ar_1$, $Ar_2$, and $Ar_3$, independently, is phenyl, thienyl, furyl, or pyrrolyl; each of $R_1$, $R_2$, $R_3$, $R_4$, $R_5$, and $R_6$, independently, is H, nitro, halogen, R, OH, OR, C(O)OH, C(O)OR, C(O)SH, C(O)SR, C(O)NH$_2$, C(O)NHR, C(O)NRR', ROH, ROR', RSH, RSR', ROC(O)R'OH, NHR, NRR', RNHR', or RNR'R''; or $R_1$ and $R_2$ together, $R_3$ and $R_4$ together, or $R_5$ and $R_6$ together are ORO; wherein each of R, R', and R'', independently is $C_1$–$C_6$ alkyl; and n is 1, 2, or 3. The compound is in an effective amount for enhancing learning and memory or treating amnesia.

9 Claims, No Drawings

ENHANCEMENT OF LEARNING AND MEMORY AND TREATMENT OF AMNESIA

RELATED APPLICATIONS

This application claims priority to U.S. provisional application No. 60/322,389 filed on Sep. 14, 2001.

BACKGROUND

Long-term potentiation (LTP) is a long-lasting form of synaptic plasticity that contributes to some types of learning and memory. For review, see, e.g., Bliss & Collingridge (1993) *Nature* 361: 31–39. In the hippocampus CA1 region, induction of LTP is dependent on $Ca^{2+}$ entry into the postsynaptic neuron triggered by N-methyl-D-aspartate receptor activation. See, e.g., Tsien et al. (1996) *Cell* 87: 1327–1338. The N-methyl-D-aspartate receptor has drawn particular interest since it appears to be involved in a broad spectrum of Central Nervous System disorders. See, e.g., Foster et al. (1987) *Nature* 329: 395–396; and Mayer et al. (1990) *Trends in Pharmacol. Sci.* 11: 254–260.

Nitric oxide is a diffusible molecule that can act as a novel type of intercellular messenger in the brain and may act as a retrograde messenger during LTP. See, for example, Son et al. (1996) *Cell* 87: 1015–1023; and Wilson et al. (1997) *Nature* 386: 338. Inhibitors of nitric oxide synthase, the enzyme for nitric oxide production, can prevent induction of LTP. One of the downstream effectors of nitric oxide is cGMP, which is also involved in the induction of LTP. cGMP is generated by a soluble guanylyl cyclase. Inhibitors of the soluble guanylyl cyclase suppress LTP. See, for example, Zhuo et al. (1994) *Nature* 368: 635–639; and Boulton et al. (1995) *Neuroscience* 69: 699–703. In addition, cGMP controls activities of many proteins, including cGMP-dependent protein kinase G, which may play a role in the induction of LTP. Inhibitors of protein kinase G block induction of LTP, and activators of protein kinase G facilitate the LTP induction in response to weak tetanic stimuli. See, for example, Zhuo et al. (1994) *Nature* 368: 635–639. Zhuo et al. (1994) *Nature* 368:, 635–639. Accordingly, a signaling pathway including nitric oxide, cGMP, and protein kinase G is involved in induction of LTP. Identification of compounds that modulate the signaling pathway could provide new therapeutics useful in enhancing learning and memory.

SUMMARY

In one respect, this invention features a method for enhancing learning and memory. The method includes administrating to a subject in need thereof a fused pyrazolyl compound of the formula (I):

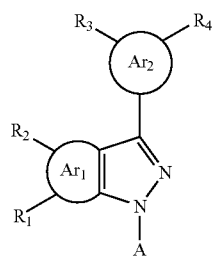

(I)

A is H, R, or

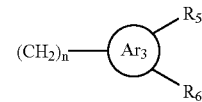

(referred to as "$(CH_2)_n Ar_3(R_5)(R_6)$" hereinafter); each of $Ar_1$, $Ar_2$, and $Ar_3$, independently, is phenyl, thienyl, furyl, or pyrrolyl; each of $R_1$, $R_2$, $R_3$, $R_4$, $R_5$, and $R_6$, independently, is H, nitro, halogen, R, OH, OR, C(O)OH, C(O)OR, C(O)SH, C(O)SR, C(O)NH_2, C(O)NHR, C(O)NRR', ROH, ROR', RSH, RSR', ROC(O)R'OH, NHR, NRR', RNHR', or RNR'R"; or $R_1$ and $R_2$ together, $R_3$ and $R_4$ together, or $R_5$ and $R_6$ together are ORO. Each of R, R', and R", independently is $C_1$–$C_6$ alkyl; and n is 1, 2, or 3. The compound is in an effective amount for enhancing learning and memory.

Formula (I) includes a pyrazolyl core and at least two aryl groups, i.e., $Ar_1$ and $Ar_2$. A subset of the compounds of formula (I) are featured by that A is $(CH_2)_n Ar_3(R_5)(R_6)$. For example, $Ar_1$ is phenyl, and $R_1$ and $R_2$ are substituted at positions 4 and 5 of the phenyl group, respectively. $Ar_2$ can be 5'-furyl, and one of $R_3$ and $R_4$ is substituted at position 2 of the 5'-furyl group, e.g., 1-benzyl-3-(5'-hydroxymethyl-2'-furyl)-indazole (Compound 1). $Ar_2$ can also be phenyl, and one of $R_3$ and $R_4$ is substituted at position 4 of the phenyl group, e.g., 1-(3-chloro-benzyl)-3-(4'-tolyl)-indazole (Compound 9) or 1-(4-nitro-benzyl)-3-(4'-tolyl)-indazole (Compound 10). In some embodiments, $Ar_3$ is phenyl, and n is 1.

Another subset of the compounds of formula (I) are featured by that A is H. For example, $Ar_1$ is phenyl, and $R_1$ and $R_2$ are substituted at positions 4 and 5 of the phenyl group, respectively. In another example, $Ar_2$ is 5'-furyl, and one of $R_3$ and $R_4$ is substituted at position 2 of the 5'-furyl group.

The term "aryl" as used herein includes phenyl, thienyl, furyl, or pyrrolyl, each of which optionally includes one or more substituted moieties. The substituted moieties may be the same as or different from $R_1$, $R_2$, $R_3$, $R_4$, $R_5$, or $R_6$. They can be halogen, amino, hydroxyl, mercapto, cyano, nitro, $C_1$–$C_6$ alkyl, $C_1$–$C_6$ alkenyl, $C_1$–$C_6$ alkoxy, aryl, heteroaryl, or heterocyclyl, wherein alkyl, alkenyl, alkoxy, aryl, heteroaryl, and heterocyclyl are optionally substituted with $C_1$–$C_6$ alkyl, halogen, amino, hydroxyl, mercapto, cyano, or nitro. The term "alkyl" refers to both linear alkyl and branched alkyl.

Set forth below are some specific examples of the fused pyrazolyl compounds which can be used to practice the method of this invention:

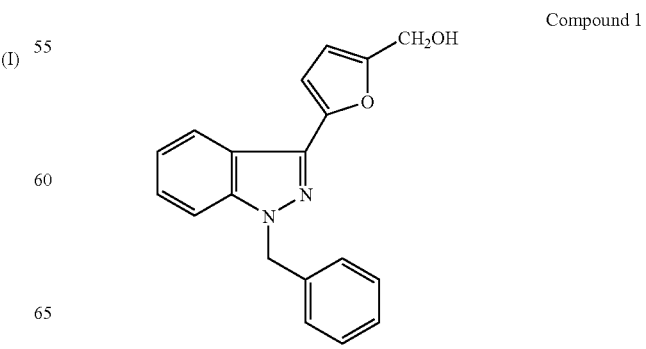

Compound 1

-continued
Compound 2:
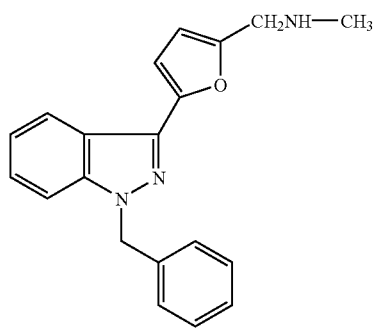
Compound 3:
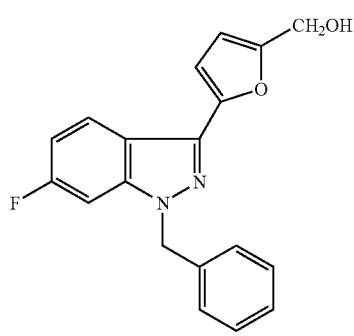
Compound 4:
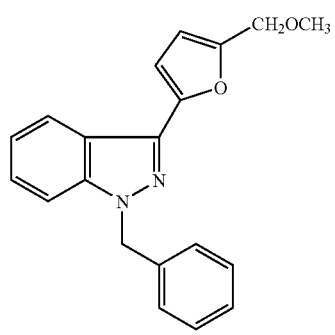
Compound 5:
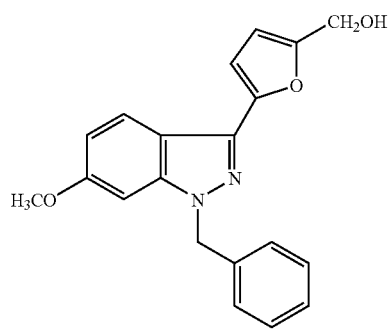
Compound 6:
-continued
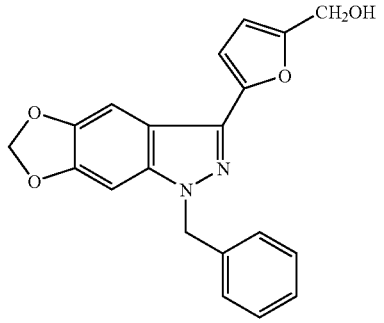
Compound 7:
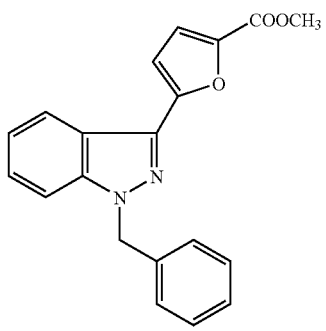
Compound 8:
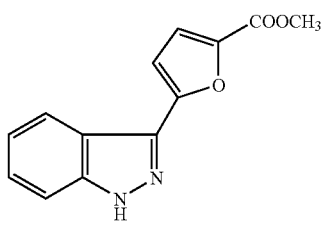
Compound 9:
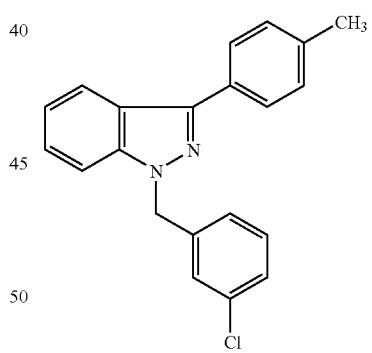
Compound 10:
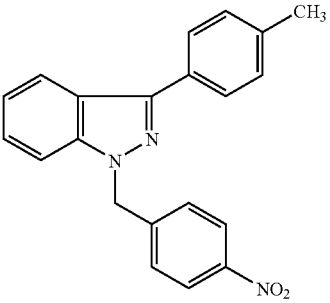

-continued

Compound 11:

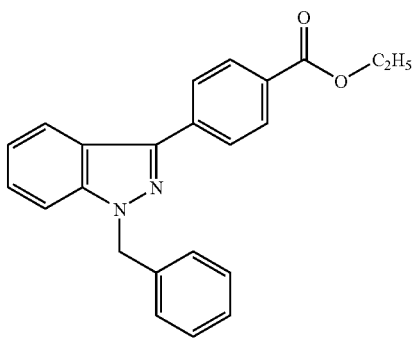

Compound 12:

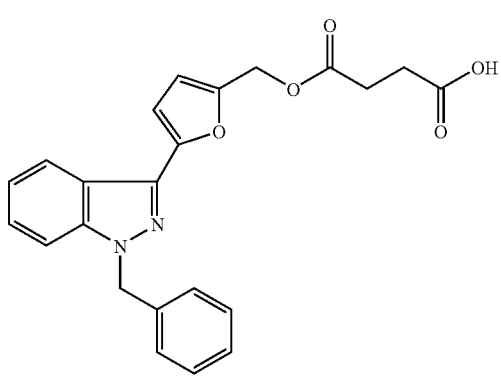

Compound 13:

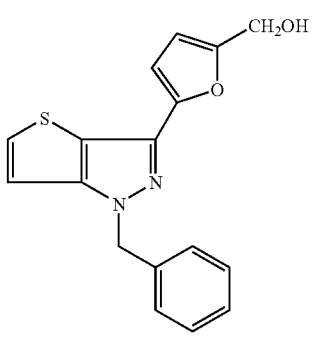

Compound 14:

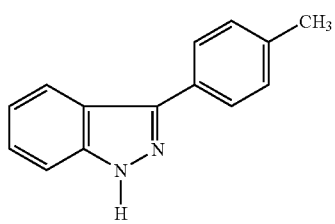

-continued

Compound 15:

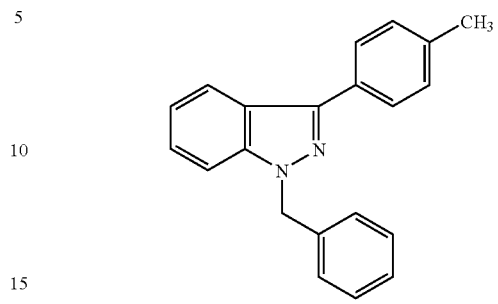

Compound 16:

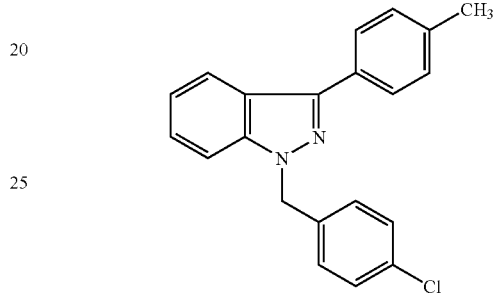

Compound 17:

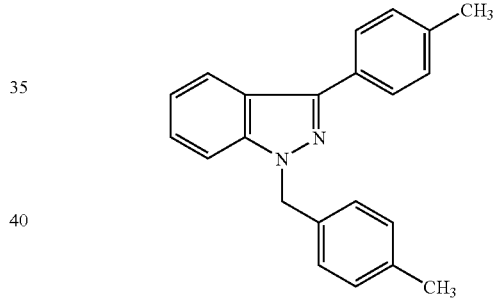

Compound 18:

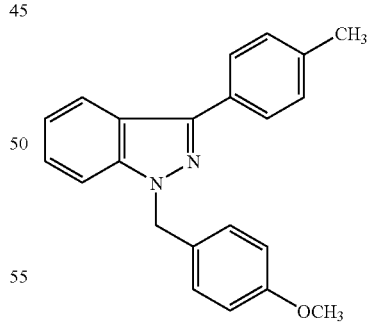

The fused pyrazolyl compounds described above include the compounds themselves, as well as their salts and their prodrugs, if applicable. Such salts, for example, can be formed by interaction between a negatively charged substituent (e.g., carboxylate) on a fused pyrazolyl compound and a cation. Suitable cations include, but are not limited to, sodium ion, potassium ion, magnesium ion, calcium ion, and an ammonium cation such as teteramethylammonium ion. Likewise, a positively charged substituent (e.g., amino) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing fused pyrazolyl compounds described above.

This invention also features a method for treating amnesia. The method includes administering an effective amount of one or more of the fused pyrazolyl compounds described above to a subject in need thereof. As used herein, amnesia refers to loss of memory. It may result from neuropsychological disorders. Examples of "neuropsychological disorders" include, but are not limited to, cognitive, learning, and memory deficits, disorders derived from neurodegenerative disorders (e.g., Huntington's disease, Parkinson's disease, or Alzheimer's disease), mood disorders (e.g., bipolar disorder, dysthymia, or seasonal effective disorder), and depression.

In another aspect, this invention features a packaged product. The packaged product includes a container, one or more fused pyrazolyl compounds in the container, and a legend (e.g., a label or an insert) associated with the container and indicating administration of the pyrazolyl compounds for enhancing learning and memory or for treating amnesia.

Also within the scope of this invention is the use of the above-described compounds for the manufacture of a medicament for enhancing learning and memory, or for treating amnesia.

Other features, objects, and advantages of the invention will be apparent from the description and from the claims.

DETAILED DESCRIPTION

A fused pyrazolyl compound used to practice the method of this invention can be prepared by procedures well known to a skilled person in the art (see, e.g., U.S. Pat. No. 5,574,168). They include the following synthetic route: An aryl aryl ketone is first prepared by coupling an arylcarbonyl chloride with another aryl compound. Either aryl compound is optionally mono- or multi-substituted. The ketone then reacts with an arylalkylhydrazine, the aryl group of which is also optionally mono- or multi-substituted, to form a hydrazone containing three aryl groups. The hydrazone group is transformed into a fused pyrazolyl core via an alkylene linker, another aryl group is fused at 4-C and 5-C of the pyrazolyl core, and the third aryl group is directly connected to 3-C of the pyrazolyl core. Derivatives of the fused pyrazolyl compound may be obtained by modifying the substituents on any of the aryl groups.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the fused pyrazolyl compound. In addition, various synthetic steps may be performed in an alternate sequence or order to give the desired compounds. Synthetic chemistry transformations and protecting group methodologies (protection and deprotection) useful in synthesizing applicable fused pyrazolyl compounds are known in the art and include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995) and subsequent editions thereof.

A fused pyrazolyl compound thus synthesized can be further purified by a method such as column chromatography, high pressure liquid chromatography, or recrystallization.

One aspect of this invention is a method for enhancing learning and memory or treating amnesia that is derived from neuropsychological disorders. The method includes administering to a subject in need thereof an effective amount of one or more fused pyrazolyl compounds and a pharmaceutically acceptable carrier. As used herein, the term "memory" refers to the capability of the mind to store up conscious processes and reproduce them later with some degree of fidelity. As a psychological process, memory includes retention, reproduction, and recognition. Theoretical models of memory include a sensory register, short-term memory, working memory, and long-term memory (including semantic memory, procedural memory, and episodic memory). Other conceptualizations of memory include auditory memory, visual memory, motor memory, and recognition memory. The term "treating" is defined as the application or administration of a composition including a fused pyrazolyl compound to a subject, who has amnesia derived from neuropsychological disorders, a symptom of amnesia or a predisposition toward amnesia, with the purpose to cure, heal, alleviate, relieve, alter, remedy, ameliorate, improve, or affect amnesia, the symptoms of amnesia or the predisposition toward amnesia. "An effective amount" is defined as the amount of a fused pyrazolyl compound which, upon administration to a subject in need thereof, is required to confer therapeutic effect on the subject. An effective amount of a fused pyrazolyl compound may range from about 0.01 mg/kg to about 300 mg/kg. Effective doses also vary, as recognized by those skilled in the art, depending on route of administration, excipient usage, and the possibility of co-usage with other agents for enhancing learning and memory, or with other agents for treating amnesia.

To practice the method of the present invention, a fused pyrazolyl compound can be administered orally, parenterally, by inhalation spray or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

A carrier in a pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the fused pyrazolyl compound, or one or more solubilizing agents, can be utilized as pharmaceutical excipients for delivery of the fused pyrazolyl compound. Examples of other carriers include colloidal silicon dioxide, magnesium stearate, cellulose, sodium lauryl sulfate, and D&C Yellow #10.

A suitable in vitro assay can be used to preliminarily evaluate a fused pyrazolyl compound's ability to increase long-term potentiation induction. In vivo screening can also be performed by following procedures well known in the art. See the specific examples below.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

Synthesis of 1-benzyl-3-(5'-hydroxymethyl-2'-furyl)-indazole (Compound 1)

Calcium borohydride was first prepared by stirring anhydrous calcium chloride (88.8 mg, 0.8 mmole) with sodium borohydride (60 mg, 1.6 mmole) in anhydrous THF (20 mL) for 4 hrs. Then a 30 mL THF solution containing 88.0 mg 1-benzyl-3-(5'-methoxycarbonyl-2'-furyl)-indazole (0.27 mmole) was added dropwise to the calcium borohydride solution at 30±2° C. The mixture was heated under reflux for 6 hrs, cooled, quenched into crushed ice, placed at a reduced pressure to remove THF, and filtered to obtain a solid product. The solid was extracted with dichloromethane. The extract was concentrated to 50 mL and a solid precipitated after petroleum ether was added. The precipitate was collected and purified by column chromatography (silica gel-benzene) to obtain 70.0 mg 1-benzyl-3-(5'-hydroxymethyl-2'-furyl)-indazole at a yield of 87%.

mp: 108–109° C. MS (%), m/z: 304 (M+). IR (KBr) $v_{max}$: 3350 $cm^{-1}$ (—OH). $^1$H-NMR (DMSO-$d_6$, 200 MHz) δ: 4.51 (2H, d, J=5.5 Hz, —$CH_2O$—), 5.31 (1H, t, J=5.5 Hz, —OH), 5.70 (2H, s, ~$NCH_2$-), 6.48 (1H, d, J=3.4 Hz, H-4'), 6.97 (1H, d, J=3.4 Hz, H-3'), 7.21–7.31 (6H, m, H-5, phenyl), 7.45 (1H, t, J=8.2 Hz, H-6), 7.75 (1H, dd, J=8.2, 1.8 Hz, H-7), 8.12 (1H, dd, J=8.2. 1.0 Hz. C4-H).

Electrophysiology Tests

After decapitation, brains of either adult (150–250 mg, for the induction of long-term potentiation) or young (2–3 weeks old, for the induction of long-term depression) Wistar rats were rapidly removed, and the hippocampus was dissected out. Transverse hippocampal slices (450 μm thickness) were immediately placed in an ice-cold cutting buffer containing 124 mM NaCl, 3 mM KCl, 1.0 mM $Na_2HPO_4$, 25 mM $NaHCO_3$, 0.5 mM $CaCl_2$, 5.0 mM $MgSO_4$, 10 mM glucose, saturated with 95% $O_2$ and 5% $CO_2$. The slices were then maintained in an interface chamber at room temperature, and perfused at flow rate of 1–2 mL/min with artificial cerebrospinal fluid (ACSF). The composition of ACSF contained 124 mM NaCl, 4.4 mM KCl, 1.0 mM $Na_2HPO_4$, 25 mM $NaHCO_3$, 2.0 mM or 2.5 mM $CaCl_2$, 1.0 mM $MgSO_4$, 10 mM glucose, gassed with 95% $O_2$ and 5% $CO_2$. The field Excitatory Postsynaptic Potentials (fEPSP) was evoked by test pulses through a bipolar stimulating electrode placed on the Schaffer collateral/commissural pathway, and recorded from the stratum radiatum of CA1 using a glass micropipette electrode (5–10 MΩ) filled with 2 M NaCl. The test pulse duration was 100 μsec, and test responses were elicited at 0.02 Hz. To record field potentials in the cortico-amygdala pathway, a stimulating electrode was placed in the external capsule, which contained fibers from the auditory cortex to the lateral amygdala. Bicuculine (10 μM) was present in the perfusion solution when the fEPSPs of amygdala were recorded. To increase the effectiveness of fused pyrazolyl compounds that were applied through the perfusion system, the ACSF level in the recording chamber was sufficiently high to cover the hippocampal slices but not to float them. All fused pyrazolyl compounds were perfused in ACSF.

Evoked fEPSPs were recorded and data were analyzed. The initial slope of the fEPSPs was calculated, and the data were expressed as percentages of the average of the baseline slope of the fEPSPs.

Long-term potentiation (LTP) enhanced by Compound 1: LTP is the most prevailing neurophysiological model for learning and memory. LTP in the Schaffer collateral-CA1 pathway of rat hippocampal slices was induced by strong tetanic stimulation, which consists of two 100 Hz, 1 sec trains delivered 20 sec apart. The strong tetanus induced LTP in the slope of the fEPSP 163.4±7.0% (n=6) at 50 min after the tetanus. LTP was markedly enhanced by perfusion with Compound 1 (1.6 μM) for 6 min (3 min before and 3 min after the tetanus). The fEPSP slope was 404.7±34.9% (n=5) at 50 min after the tetanus.

Weak tetanic stimulation which did not induce LTP consisted of a 20 Hz, 0.5 sec train. Unexpectedly, perfusion with Compound 1 (1.6 μM) for 6 min (3 min before and 3 min after the tetanus) induced LTP. The fEPSP slope was 172.9±10.7% (n=7) at 1 hr. Three trains (100 Hz, 1 sec at 3 min interval) of stimulation induced a transient potentiation that decayed to baseline within 30 min in amygdala. However, the same trains of stimulation induced an enduring LTP that lasts stably for at least 1 hr in the presence of compound 1 (n=4).

Mechanism of Compound 1 on LTP enhancement: The role of nitric oxide was investigated. Concomitant perfusion with Compound 1 and $N^G$-nitro-L-arginine-methylester (L-NAME, purchased from RBI) (300 μM), a nitric oxide synthase inhibitor, significantly attenuated LTP induced by Compound 1. On the other hand, Zinc protoporphyrin (1 μM), a heme oxygenase inhibitor, did not affect LTP induced by Compound 1. The results indicate that nitric oxide but not carbon monoxide is involved in the Compound 1-enhanced LTP induction.

Compound 1 was co-perfused with 1 H-[1,2,4]diazolo[4,3,-a]quinoxalin-1-one (ODQ, purchased from TOCRIS), a specific inhibitor of a soluble guanylyl cyclase. Without ODQ, LTP was induced by Compound 1 at weak tetanus (50 Hz/0.5 s). With ODQ (5 μM), LTP was not induced by Compound 1. The fEPSP slope was 107.8±3.9% (n=5). The results indicate that the soluble guanylyl cyclase is involved in the Compound 1-enhanced LTP induction.

Compound 1 was also co-perfused with KT5823 (from Calbiochem), a specific inhibitor of a protein kinase G. Without KT5823, LTP was induced by Compound 1 at weak tetanus (50 Hz/0.5 s). With KT 5823 (2 μM), the LTP induced by Compound 1 was inhibited. The fEPSP slope was 112.9±5.4% (n=4). The results suggest that the nitric oxide-cGMP-protein kinase G-signaling pathway is involved in the Compound 1-enhanced LTP induction.

Compound 1 was further co-perfused with 2-amino-5-phosphonopentanoic acid (AP5, purchased from RBI), a N-methyl-D-aspartate receptor antagonist. Without AP5, LTP was induced by Compound 1 at weak tetanus (50 Hz/0.5 s). With AP5 (100 μM), the LTP induced by Compound 1 was delayed. The fEPSP slope was 142.1±13.5% (n=5). The results suggest that $Ca^{2+}$ influx from N-methyl-D-aspartate receptor plays a role is involved in the Compound 1-enhanced LTP induction.

In addition, Compound 1 was co-perfused with MCPG ((±)-α-methyl-(4-carboxyphenyl)glycine; from Sigma/RBI), a metabotropic receptor. With MCPG (100 μM), the LTP induced by Compound was reduced. Simultaneous application of AP-5 and MCGP inhibited the LTP induced by Compound 1. The fEPSP slope was 111.5±12.3% (n=3).

LTP was not further potentiated by Compound 1 when Compound 1 was added to the ACSF (at 1.6 μM) 10 min after 2 trains of strong tetanus (100 Hz/1 sec), suggesting that nitric oxide is released upon high frequency stimulation and the Compound 1-enhanced LTP induction occurred only within a few minutes after the tetanization.

Compound 1 on plasticity induced by low-frequency stimulation (LFS): LFS (900 pulses at 1 Hz) was delivered to hippocampal slices taken from young rats (7~14 day-old) to induce long-term depression (LTD). Stimulation of hippocampal slices at 1 Hz for 3 min produced no LTD of synaptic transmission. However, this short-duration LFS induced significant LTD in the presence of Compound 1 (83.4±10.9%, n=3). Perfusion of Compound 1 (1.6 μM) for 15 min during LFS reversed the LTD plasticity into LTP. A weaker electrical stimulation at 0.02 Hz was delivered in the presence of both nitric oxide donor nitroprusside (300 μM) and Compound 1 (1.6 μM). Simultaneous perfusion of the nitric oxide donor nitroprusside (30 μM) and Compound 1 (1.6 μM) induced LTD. The data suggest that nitric oxide donor is able to mimic the action of tetanic stimulation in the presence of Compound 1. Compound 1 or nitroprusside alone produced no potentiation on fEPSP at 0.02 Hz stimulation.

Enhancement of LTP by pyrazolylcompounds: Compounds 1–8 were also tested to enhance LTP induction in hippocampal slices. The results are shown in Table 1. The fEPSP slopes 60 min after tetanus (50 Hz, 0.5 s) are shown. Each compound (1.6 μM) was perfused 3 min before and 3 min after the weak tetanus.

TABLE 1

Effects of pyrazolyl compounds on the enhancement of LTP induction

| Compounds | fEPSP |
| --- | --- |
| Control | 108.4% |
| Compound 1 | 172.9% |
| Compound 2 | 165.9% |
| Compound 3 | 218.9% |
| Compound 4 | 216.9% |
| Compound 5 | 180.8% |
| Compound 6 | 260.3% |
| Compound 7 | 200.3% |
| Compound 8 | 180.6% |

Behavioral Task Tests

Morris water maze: Morris water maze was performed in a circular pool (224 cm in diameter, 46 cm in height) located in a room with distinctive visual cues. Water was filled to a depth of 36 cm and a transparent plastic platform (25×25 cm, 32 cm in height) was located at the center of a fixed quadrant. Rats were trained for two days in the task environment: free-swimming in the pool without the transparent plastic platform. Each training session was 2 min and the rats were picked up from the pool by an experimenter. Then, rats received 4 consecutive daily training trials for the following six days. During each training trial, each rat was placed into the water randomly from one of the quadrants. The rat had to swim until it climbed onto the plastic platform submerged underneath the water. The time duration from being placed into the water to climbing onto the plastic platform was recorded and defined as escape latency. If the rat failed to find the plastic platform after 120 s, it was picked up by the experimenter and placed onto the plastic platform. Each rat stayed on the platform for 60 s, which also served as the interval of trial. Compound 1 (1 mg/kg) or vehicle was daily injected to each rat 10 min before the first training trial. After the last training trial of each day, each rat was dried by a towel, and an electric heater was placed in its home cage.

Substantial evidence implicates the hippocampus in acquisition and retention of spatial information. See, e.g., Ohon et al. (1979) *Behav. Brain Sci.* 2: 316–365; and Barnes (1988) *Trend Neurosci.* 11: 163–169. The effect of Compound 1 on the acquisition of spatial memory in the Morris water maze was tested. Rats received 4 consecutive training trials every day. Compound 1 (1 mg/kg) was daily injected (i.p., 1 mg/kg) 10 min before the first trial of training. The data show that Compound 1 shortened the escape latency of 2~4 trials on the first training day, suggesting that Compound 1 promotes short-term memory. The escape latencies of 2~4 trials were 93.8±8.7 s, 79.3±12/3 s and 57.6±12.5 s for a control group, and 50.4±10.2 s, 47.3±6.8 s and 30.3±10.3 for the Compound 1 group (n=10), respectively. The escape latencies of the first trial on the following 3 training days were also markedly shortened in the Compound 1 group. The escape latencies were 91.1±9.8 s, 47.1±3.9 s and 35.3±6.1 s for the control group, and 55.4±12.8 s, 15.3±2.1 s, and 13.4±1.7 s for the Compound 1 group (n=10), respectively. These results suggest that Compound 1 also enhances long-term memory. The escape latency is shorter in the Compound 1 group throughout the whole experimental period up to 21 days although Compound 1 was only administered once for 4 days. The mean escape latency on the day-21 is 13.5±1.8 s and 6.0±0.5 s (n=10 each) for the control group and the Compound 1 group, respectively. From results shown above, Compound 1 is a promising drug for improving learning and memory. Compound 1 was mixed with 1.25% carboxymethylcellulose (CMC) and orally delivered to stomach (10 mg/kg) directly 30 min before the first trial for 6 successive days. Similar to injected administration, oral administration of Compound 1 also promoted short-term and long-term memory.

Since L-NAME antagonized Compound 1-induced LTP enhancement in hippocampal slices, in vivo experiments were performed to test the effect of L-NAME on the improved learning and memory provoked by Compound 1. In these experiments, rats chronically implanted with cannulae were injected intracerebroventrically with L-NAME (1 mmole/10 mL) or saline 10 min before the first trial of daily training, concomitant with i.p. injection of Compound 1 (1 mg/kg). The data show that L-NAME caused profound amnesia of the task and significantly blocked the enhanced learning and memory induced by Compound 1. Intracerebroventricular administration of KT 5823 also impaired the Compound 1-induced enhancement.

Passive Avoidance and active avoidance task: Rats were trained and tested on a one-trial step-through passive inhibitory avoidance task with a procedure as described in Liang et al. (1998, *Chin. J. Physiol.* 41: 33–44). Briefly, an apparatus was a trough-shape alley divided by a sliding door into a well-lit safe compartment and a dark shock compartment. A rat was placed in the lit side facing away from the door. As the rat turned around, the door was opened. After the rat stepped into the dark compartment, it received an inescapable footshock via a constant current shocker controlled by a timer (Lafayette Instruments, Model 80240 and Model 58010, Indiana, USA). After administration of the foot-shock, the rat was removed from the alley and returned to its home cage. In a retention test given 24 hrs or 10 days later, the rat was reintroduced into the alley and the latency of stepping into the shock compartment with all four feet was taken as a retention score. If a rat did not step through in 5 or 10 min, the test trial was terminated and a ceiling score of 300 s or 600 s was assigned.

The amygdala is also implicated in learning and memory. Studies have shown that this brain structure is particularly involved in processing affective information. See, e.g., Cahill and McGaugh (1990) *Behav. Neurosci.* 104: 532–543; and Gilbert et al. (1991) *Behav. Neurosci.* 105: 533–561. It has been reported that nitric oxide is also involved in activity-dependent synaptic plasticity and passive avoidance learning in amygdaloid nucleus. See, e.g., Bernabeu et al. (1995) *NeuroReport* 6: 1498–1500; Watanabe et al. (1995) *Brain Res.* 688: 233–236; and Teledgy and Kokavszky (1997) *Neuropharmacology* 36: 1583–1587. The effect of Compound 1 on passive avoidance learning was studied. Compound 1 was injected (i.p., 1 mg/kg) 10 min before foot-shock training. The results show that Compound 1 markedly prolonged the retention latencies in the lighted compartment. The memory lasts for several days. The retention scores were very high even if tested on day 10. There were much more rats which had retention latencies longer than 5 min in Compound 1-treated rats (2 out of 15 in a control group and 11 out of 12 in a Compound 1-treated group, respectively) tested on both day-1 and day-10. When the Compound 1 was mixed with 1.25% CMC and delivered to stomach directly (10 mg/kg) before foot-shock. The retention test was performed 1 day and 10 days later, respectively. Compound 1 greatly improved passive avoidance learning (Table 2). As shown in Table 3, Compound 1 (i.p., 1 mg/kg) promoted learning behavior in aged rats although the effect is much less pronounced than in younger rats. Rats of 1-year-old were chosen for this experiment. Compound 1 (1 mg/kg) was i.p. injected 10 min before foot-shock. The retention test was performed 1 day and 10 days later, respectively.

TABLE 2

Enhancement of oral Compound 1 on the retention in a passive avoidance task.
Retention Scores (sec)

|  | Day-1 | Day-10 |
| --- | --- | --- |
| Control | 54.9 | 224.1 |
|  | 59.0 | >600 |
|  | 200.8 | >600 |
|  | >600 | >600 |
|  | 12.3 | 24.7 |
|  | 150.1 | 143.2 |
|  | 12.3 | 12.1 |
|  | >300 | 543.4 |
|  | 24.7 | 24.3 |
|  | mean ± std 157.1 ± 64.3 | 308.0 ± 90.8 |
| Compound 1 | >600 | 454.0 |
|  | >600 | >600 |
|  | >600 | >600 |
|  | >600 | >600 |
|  | 15.0 | 15.0 |
|  | >300 | 207.1 |
|  | >300 | 453.2 |
|  | >300 | >600 |
|  | >300 | 343.2 |
|  | 77.1 | 500.2 |
|  | mean ± std 369.2 ± 70.2 | 437.3 ± 62.4 |

TABLE 3

Enhancement of injected Compound 1 on the retention in a passive avoidance task in aged rat.
Retention Scores (sec)

|  | Day-1 | Day-10 |
| --- | --- | --- |
| Control | 18.1 | 5.4 |
|  | 4.2 | 2.2 |
|  | >300 | >300 |
|  | 74.7 | 58.5 |
|  | 47.3 | 156.9 |
|  | mean ± std 88.9 ± 54.2 | 104.6 ± 56.3 |
| Compound 1 | >300 | 252.2 |
|  | >300 | 255.9 |
|  | 207.1 | 85.8 |
|  | >300 | >300 |
|  | 58.1 | 12.9 |
|  | mean ± std 233.0 ± 47.3 | 181.4 ± 55.7 |

From results shown above, Compound 1 can improve the learning of passive avoidance in both young and aged rats. In these tasks, Compound 1 preferentially affects the acquisition of newly-formed memory, a process which is thought to be related to the induction phase of LTP. Foot-shock is thought to be a great stimulation to rats. Nitric oxide is supposed to be released under this situation and quickly metabolized. Compound 1 did not exert any effect on rats when Compound 1 was injected 30 min after foot-shock. These results suggest that Compound 1 can improve learning behavior only it was administered before or during the memory tasks.

The data also showed that Compound 1 did not exert any effect on rat avoidance behavior when it was injected 30 min after foot-shock. In addition, the enhancement effect induced by Compound 1 was significantly antagonized by L-NAME and KT5823 (i.c.v., 1 mmole and 0.2 nmole, respectively). These results suggest that Compound 1 can improve learning behaviors only when it was administered before or during the memory tasks. Furthermore, Compound 1 administered 10 min before the context training instead of the administration of foot-shock prolonged the retention scores of passive inhibitory avoidance, suggesting that Compound 1 enhanced the acquisition of memory for environmental cues without foot-shock.

For the test of active avoidance, the rat was placed in the dark compartment, facing the door. The door was opened halfway, and the rat had 10 sec to shuttle over the door to lit compartment. Rat was not chosen for this experiment if the rat crossed to the safe side within 10 sec. Foot-shock was turned on at 10 s later. Rat escaped into safe compartment and the door was closed. The retention time on dark shock compartment was measured 48 hr later. The rats were discarded once the rats enter lit compartment within 10 s on the day of context training. Foot-shock was administered 10 s after putting in the dark compartment on day-1. Memory retention was tested on day-2. Injection of Compound 1, 10 min before foot-shock caused noticeable increase in the retention of memory and decrease in the escape latency from the shock- to the safe-compartment. Furthermore, the memory enhancement effect induced by Compound 1 was effectively inhibited by L-NAME and KT5823 (i.c.v., 1 mmole and 0.2 nmole, respectively). Thus, Compound 1 significantly improves learning behaviors of rats in both passive avoidance and active avoidance tests via NO-cGMP-PKG pathway.

Rotorod Test: This experiment was performed with mice (male, 20–25 gm). A rotorod apparatus was a plastic cylindrical rod (3 cm in diameter×13 cm in length). The rod was supported at the ends by two walls and was 25 cm from the base of the walls. The walls at the ends of the rod were high enough so that the mice cannot climb off the rod. Three trials were performed for each experiment. Compound 1 (1 mg/kg) or vehicle was i.p. injected 20 min before the first trial. For each trial of the rotorod test, the mice were placed on the rod and timed until they fell off the rod. They were timed up to a maximum of 3 min. The interval was 10 min. The rod was turned by an electric motor at 28 rpm.

Cerebellar nitric oxide has been also reported to be involved in LTD and motor learning. See, e.g., Li et al. (1995) *J. Neurophysiol.* 74: 489–494. Compound 1 improving motor learning was studied. Mice were chosen for this kind of experiment. Compound 1 (i.p., 1 mg/kg) significantly improved motor coordination of mice on a turning rotorod (28 rpm). The performance of control mice got improvement with increasing trial numbers, with a better improvement at the third trial. However, mice treated with Compound 1 showed good balance on the rod even if at first trial, and got very good motor coordination at second trial. It is obvious that Compound 1 can also improve motor learning by mainly acting on the cerebellum.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, a compound structurally analogous to a fused pyrazolyl compound can also be used to practice the present invention. Thus, other embodiments are also within the claims.

What is claimed is:

1. A method for treating amnesia, comprising administrating to a subject in need thereof an amount effective to treat amnesia of a compound of the formula:

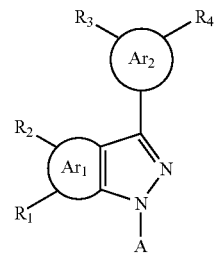

wherein

A is H, R, or

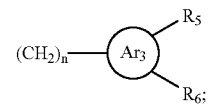

$Ar_1$ is phenyl;

each of $Ar_2$ and $Ar_3$, independently, is phenyl, thienyl, furyl, or pyrrolyl;

each of $R_1$, $R_2$, $R_3$, $R_4$, $R_5$, and $R_6$, independently, is H, nitro, halogen, R, OH, OR, C(O)OH, C(O)OR, C(O)SH, C(O)SR, C(O)NH$_2$, C(O)NHR, C(O)NRR', ROH, ROR', RSH, RSR', ROC(O)R'OH, NHR, NRR', RNHR', or RNR'R"; or $R_1$ and $R_2$ together, R3 and $R_4$ together, or $R_5$ and $R_6$ together are ORO; wherein each of R, R', and R", independently is $C_1$~$C_6$ alkyl; and n is 1, 2, or 3.

2. The method of claim 1, wherein A is

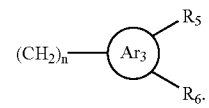

3. The method of claim 2, wherein $Ar_2$ is 5'-furyl.
4. The method of claim 3, wherein $Ar_3$ is phenyl.
5. The method of claim 4, wherein n is 1.
6. The method of claim 2, wherein $Ar_2$ is phenyl.
7. The method of claim 2, wherein A is H.
8. The method of claim 2, wherein one of $R_3$ and $R_4$ is R, C(O)OR, RNHR'.
9. The method of claim 2, wherein one of $R_1$ and $R_2$ is OR, halogen, or $R_1$ and $R_2$ together are ORO.

* * * * *